(12) United States Patent
Chiang et al.

(10) Patent No.: US 9,005,444 B2
(45) Date of Patent: Apr. 14, 2015

(54) SEPARATION OF REBAUDIOSIDE A FROM STEVIA GLYCOSIDES USING CHROMATOGRAPHY

(75) Inventors: Chen-Chou Chiang, Plymouth, MN (US); Jeffrey C. Evans, St. Michael, MN (US); John Joseph Hahn, Maple Grove, MN (US); An Amanda Jules Heylen, Zemst (BE); Andrew Keith Ohmes, Jordan, MN (US); Alexander Patist, Shakopee, MN (US); Troy Allen Rhonemus, Plymouth, MN (US); Jenna Stangler, Otsego, MN (US); Christopher Austin Tyler, Minnetonka, MN (US); Ronny Leontina Marcel Vercauteren, Beveren (BE)

(73) Assignee: Cargill, Incorporated, Wayzata, MN (US)

( * ) Notice: Subject to any disclaimer, the term of this patent is extended or adjusted under 35 U.S.C. 154(b) by 843 days.

(21) Appl. No.: 12/992,843

(22) PCT Filed: May 13, 2009

(86) PCT No.: PCT/US2009/043799
§ 371 (c)(1),
(2), (4) Date: Nov. 15, 2010

(87) PCT Pub. No.: WO2009/140394
PCT Pub. Date: Nov. 19, 2009

(65) Prior Publication Data
US 2011/0087011 A1     Apr. 14, 2011

Related U.S. Application Data

(60) Provisional application No. 61/127,382, filed on May 13, 2008.

(51) Int. Cl.
C07H 1/08 (2006.01)

(52) U.S. Cl.
CPC ..................................... C07H 1/08 (2013.01)

(58) Field of Classification Search
CPC ..................................................... C07H 1/08
USPC ............ 210/635, 656, 198.2, 502.1; 426/548; 536/18.1
See application file for complete search history.

(56) References Cited

U.S. PATENT DOCUMENTS

| 4,353,889 A | 10/1982 | DuBois |
| 4,361,697 A | 11/1982 | Dobberstein et al. |

(Continued)

FOREIGN PATENT DOCUMENTS

| CN | 1078217 C | 1/2002 |
| JP | 54041898 A | 4/1979 |

(Continued)

OTHER PUBLICATIONS

Nikolova-Damyanova et al., "Separation and quantilalio n of slevioside and rebaudioside A plant extract by normal phase high performance liquid chromatography and thin layer chromatography: a comparison," Phytochemical Analysl s, 1994 vol. 5, pp. 81-85.

*Primary Examiner* — Ernest G Therkorn (57) ABSTRACT

Disclosed are methods for the chromatographic separation of rebaudioside A from stevioside in glycoside solutions that are derived from stevia. The chromatographic separation may be an adsorb/desorb type of chromatographic separation or a fractionation type of chromatographic separation.

21 Claims, 6 Drawing Sheets

(56) References Cited

U.S. PATENT DOCUMENTS

| | | | |
|---|---|---|---|
| 6,045,842 A * | 4/2000 | Mozaffar et al. | 426/271 |
| 6,096,870 A | 8/2000 | Mozaffar et al. | |
| 7,238,379 B2 | 7/2007 | Lang | |
| 8,129,194 B2 * | 3/2012 | Riviello | 436/161 |
| 2002/0004561 A1 * | 1/2002 | Takahashi et al. | 525/326.9 |
| 2003/0138538 A1 * | 7/2003 | Kitazume et al. | 426/548 |
| 2003/0139610 A1 | 7/2003 | Khare et al. | |
| 2006/0021939 A1 * | 2/2006 | Mallet et al. | 210/656 |
| 2006/0134292 A1 * | 6/2006 | Abelyan et al. | 426/548 |
| 2006/0142555 A1 * | 6/2006 | Jonnala et al. | 536/18.1 |
| 2008/0300402 A1 * | 12/2008 | Yang et al. | 536/128 |
| 2011/0087011 A1 * | 4/2011 | Chiang et al. | 536/18.1 |

FOREIGN PATENT DOCUMENTS

| | | |
|---|---|---|
| JP | 54041899 A | 4/1979 |
| JP | 54041900 A | 4/1979 |

* cited by examiner

SEPARATION OF REBAUDIOSIDE A FROM STEVIA GLYCOSIDES USING CHROMATOGRAPHY

CROSS-REFERENCE TO RELATED APPLICATIONS

This application claims the benefit of PCT Patent Application, Serial No. PCT/US09/43799, filed May 13, 2009, entitled SEPARATION OF REBAUDIOSIDE A FROM STEVIA GLYCOSIDES USING CHROMATOGRAPHY, which claims priority to U.S. Provisional Application Ser. No. 61/127,382, filed May 13, 2008 and entitled SEPARATION OF REBAUDIOSIDE A FROM STEVIOSIDE USING CHROMATOGRAPHY, the disclosure of which is incorporated herein by reference.

BACKGROUND

With recent initiatives to decrease the amount of simple carbohydrates in human diet, there is much incentive for development of low-calorie sweeteners. Today, most sweeteners on the market, such as sucralose, aspartame, and saccharin, are chemically derived. An interesting alternative natural sweetener is stevia, derived from the South American perennial Stevia *rebaudiana bertoni*. The sweetener is about 300 times sweeter than common sugar. What makes stevia special is that it is a natural substance that can be used to replace common sugar, and is not metabolized so it contains no calories.

The sweetness in the stevia plant is attributed to the presence of high intensity sweet glycosides. The two major glycosides found in the leaves and stems of the stevia plant are stevioside and rebaudioside A. The sweet compounds are commonly extracted from stevia and purified to produce a mixture of the two compounds. Stevioside has a bitter aftertaste, whereas rebaudioside A has more intense sweetness and little bitterness. Thus, there is a strong commercial incentive to develop a process for purification of rebaudioside A from stevioside and other sweet glycosides in order to improve the flavor quality.

SUMMARY

Figure 6:
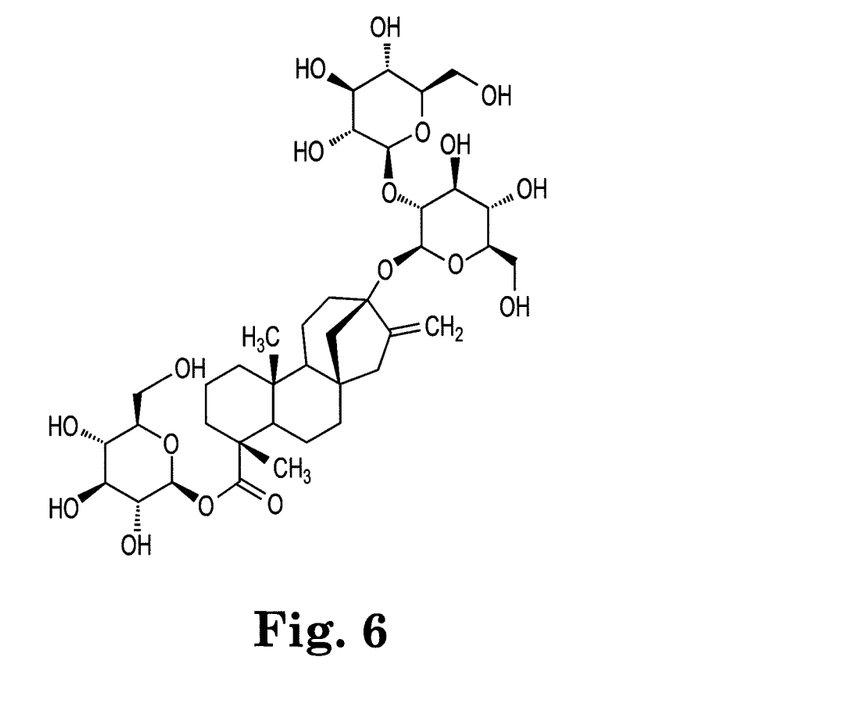
FIG. 6 is the molecular structure of stevioside.

The invention relates to the use of chromatography to separate rebaudioside A from stevioside and optionally from other glycosides (e.g., rebaudioside B and rebaudioside D) in glycoside solutions that are derived from stevia. It has been discovered that rebaudioside A can be effectively separated from stevioside and other glycosides using a chromatography process. The chromatographic processes may be an adsorb/desorb type of chromatographic separation or a fractionation type of chromatographic separation. By separation, it is not meant that the component being separated necessarily obtains 100% purity of rebaudioside A. Rather, the separated component is enriched in purity (i.e., purified) of rebaudioside A as compared to the starting composition. As used herein the term "stevioside" refers to diterpene steviol bonded to three glucose molecules. Stevioside has the molecular formula $C_{38}H_{60}O_{18}$ and has a molecular weight of 804.9 grams/mole. The chemical structure of stevioside is shown in FIG. 6.

In one aspect, the invention provides a method of separating rebaudioside A from stevioside using chromatography, the method comprising the steps of: (a) providing a glycoside solution comprising rebaudioside A; stevioside; and a solvent; (b) providing an adsorbent comprising a polystyrene divinylbenzene support functionalized with tertiary amines, quaternary amines, or both tertiary and quaternary amines; and (c) contacting the adsorbent with the glycoside solution in order to separate at least a portion of the rebaudioside A from the stevioside thereby resulting in the formation of a purified rebaudioside A solution.

In some embodiments the adsorb/desorb chromatography comprises the steps of: (a) providing a glycoside solution comprising rebaudioside A; stevioside; and a solvent; (b) providing an adsorbent comprising a polystyrene divinylbenzene support functionalized with tertiary amines, quaternary mines, or both tertiary and quaternary amines; (c) providing an elution solvent; (d) contacting the adsorbent with the glycoside solution and elution solvent so that at least a portion of the stevioside adsorbs onto the adsorbent enriching the glycoside solution in rebaudioside A and resulting in the formation of a purified rebaudioside A composition that is eluted from the adsorbent along with the elution solvent; and (d) optionally, desorbing the stevioside from the adsorbent.

In some embodiments, the elution solvent comprises about 20% weight or less ethanol and about 80% weight or greater water. For example, the elution solvent may comprise about 50% weight or less ethanol and about 50% weight or greater water.

In some embodiments the method of separating comprises fractionation chromatography, for example, using a simulated moving bed apparatus. In some embodiments, the fractionation method may comprise the steps of: (a) providing a glycoside solution comprising rebaudioside A; stevioside; and a solvent; (b) providing an adsorbent comprising a polystyrene divinylbenzene support functionalized with tertiary amines, quaternary mines, or both tertiary and quaternary amines; and (c) contacting the adsorbent with the glycoside solution so that at least a portion of the stevioside adsorbs onto the adsorbent and so that at least a portion of the rebaudioside A adsorbs onto the adsorbent; wherein the rebaudioside A propagates through the adsorbent at a faster rate than the stevioside; and (d) collecting a purified rebaudioside A solution from the adsorbent.

In some embodiments the solvent comprises about 20% weight or greater ethanol and about 80% weight or less water. In other embodiments, the solvent comprises about 25% to about 35% weight ethanol and about 65% to about 75% water.

In some embodiments the elution solvent comprises water and the adsorbent is a strongly acidic cationic exchange resin. In some embodiments the adsorbent is functionalized with tertiary amines and/or quaternary amines. The adsorbent may have a surface area of about 900 m2/gram or greater in some embodiments.

Figure 4:
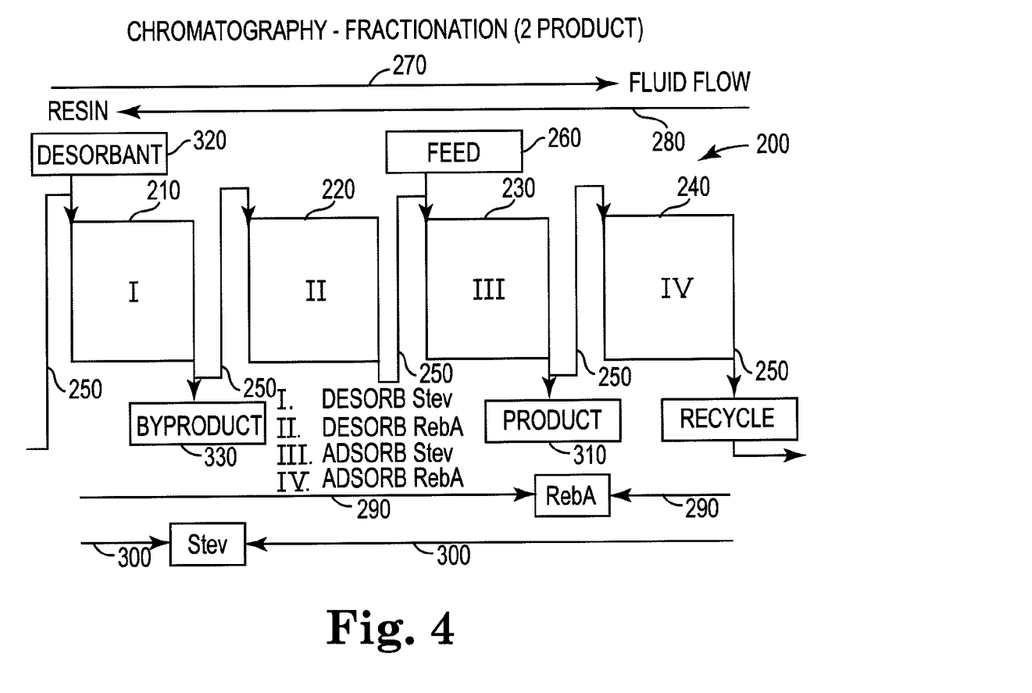
FIG. 4 is a schematic representation of a simulated moving bed fractionation separation of the invention.
Figure 5:
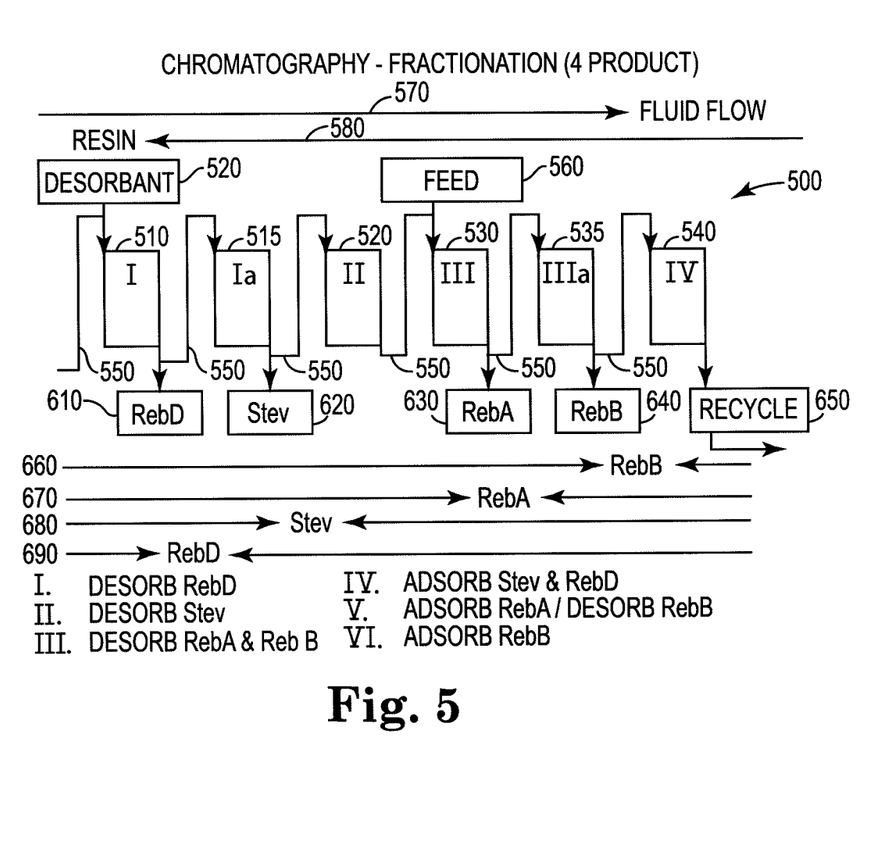
FIG. 5 is a schematic representation of a simulated moving bed fractionation separation of the invention.

Simulated moving bed chromatography may be used, for example, to separate glycoside solutions into rebaudioside A and stevioside fractions (see, FIG. 4) or into rebaudioside A, rebaudioside B, rebaudioside D, and stevioside fractions (see, FIG. 5). When rebaudioside B and D are separated from rebaudioside A and stevioside, typically the rebaudioside A propagates through the adsorbent at a faster rate than the stevioside and the rebaudioside D; and the rebaudioside B propagates through the adsorbent at faster rate than the rebaudioside A.

Methods of the invention may be used to provide a purified rebaudioside A solution that has a purity that is about 10% or greater than the purity of the glycoside solution that is used as the starting material. For example, in some embodiments, the purified rebaudioside A solution may comprise, on a dry solids basis, about 60% weight to about 99% weight rebaudioside A; or from about 60% weight to about 80% weight rebaudioside A.

BRIEF DESCRIPTION OF THE DRAWINGS

The present invention will be further explained with reference to the appended figures, wherein.

DETAILED DESCRIPTION

The invention relates to the use of chromatography to separate rebaudioside A from stevioside in glycoside solutions that are derived from stevia. It has been discovered that rebaudioside A can be effectively separated from stevioside using a chromatography process. The chromatographic processes may be an adsorb/desorb type of chromatographic separation or a fractionation type of chromatographic separation.

Adsorb/Desorb Separations:

In some embodiments of the invention, the separation takes place using an adsorb/desorb type of chromatographic separation. In an adsorb/desorb separation a first material that is to be separated from a second material preferentially adsorbs onto a solid stationary phase adsorbent, and remains bound to the stationary phase adsorbent until a desorption step is conducted. The second material does not substantially adsorb onto the stationary phase adsorbent and passes through the adsorbent. The differential in binding to the stationary phase adsorbent allows a separation to be made between the first material and the second material.

In the present invention, stevioside adsorbs strongly onto a stationary phase adsorbent comprising polystyrene divinylbenzene support that has been functionalized with tertiary amines, quaternary amines, or both tertiary and quaternary amines, whereas rebaudioside A adsorbs only weakly onto this type of stationary phase adsorbent. This allows a glycoside solution that initially comprises both stevioside and rebaudioside A to be purified (i.e., enriched) in rebaudioside A when it is passed through the stationary phase adsorbent. After performing the separation, the stationary phase adsorbent can be regenerated by desorbing the adsorbed stevioside using an appropriate desorbing solvent.

Figure 1:
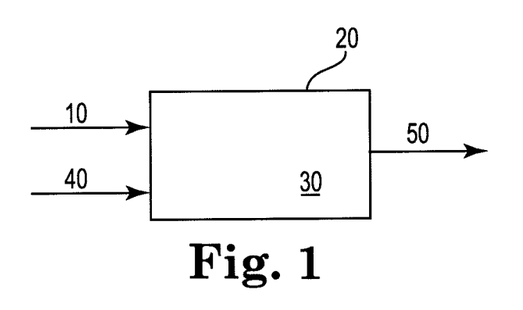
FIG. 1 is a schematic representation of an adsorb/desorb separation of the invention.
Figure 2:
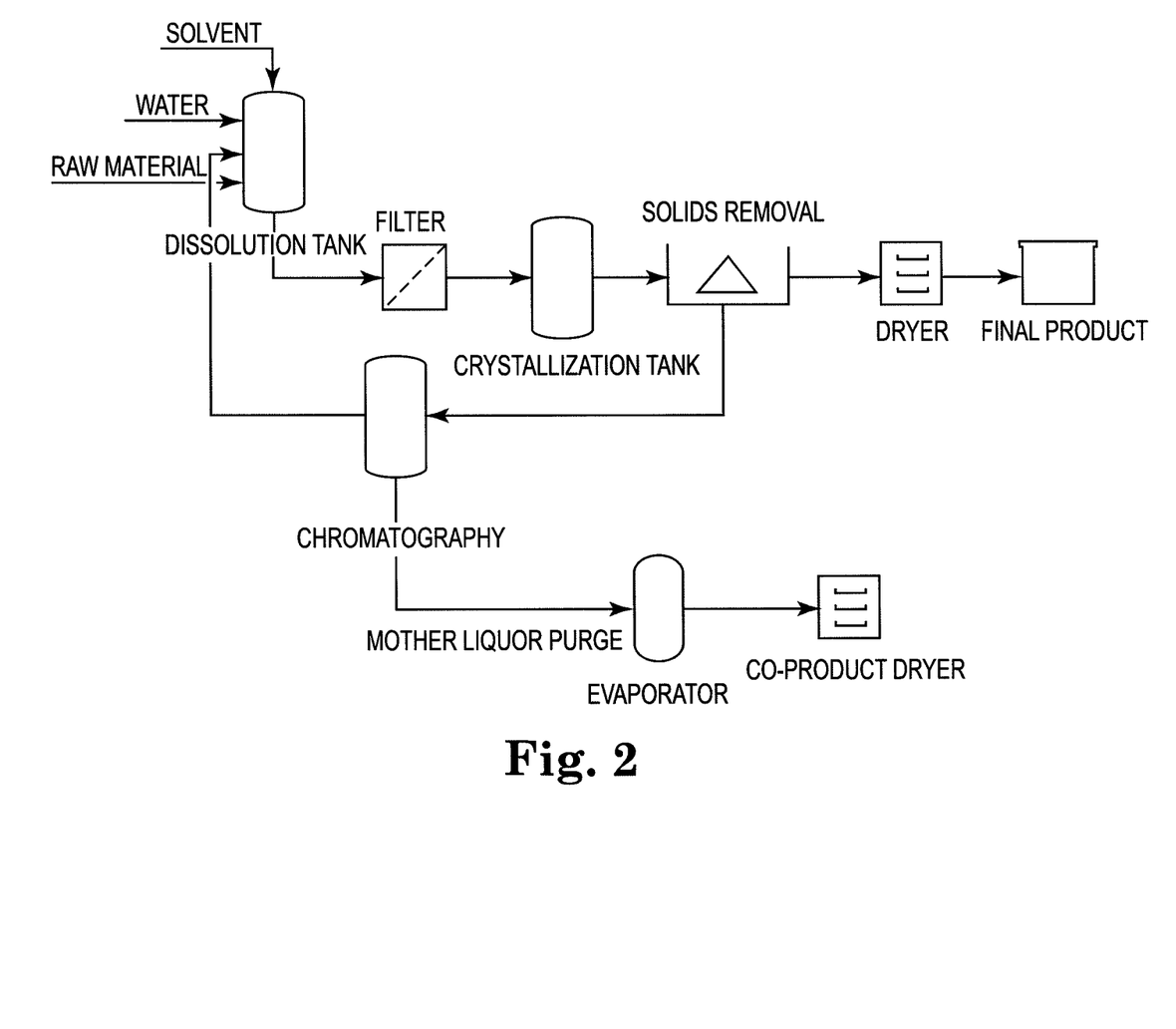
FIG. 2 is a schematic representation of a crystallization and chromatographic separation process of the invention.

An exemplary embodiment of adsorb/desorb type separation is shown in FIG. 1. In FIG. 1 a glycoside solution 10 comprising rebaudioside A and stevioside is fed to an adsorbent bed 20. The adsorbent bed 20 contains a stationary phase adsorbent 30 comprising a polystyrene support functionalized with tertiary amines, quaternary amines, or both tertiary and quaternary amines. An elution solvent 40 is fed though the adsorbent bed along with the glycoside solution 10. The elution solvent 40 functions to transport the glycoside solution 10 through the adsorbent bed 20 and the stationary phase adsorbent 30. The stationary phase adsorbent 30 preferentially adsorbs stevioside as compared to rebaudioside A, thereby enriching the elutant 50 in rebaudioside A. xxx In the method of the invention, the glycoside solution 10 may be a solution prepared from stevia after primary processing, or the glycoside solution 10 may be the mother liquor of a rebaudioside A crystallization process. In a typical crystallization process stevia is dissolved in a solvent (e.g., ethanol/water), filtered, and crystallized to form high purity rebaudioside A crystals. The mother liquor from the crystallization process which contains both rebaudioside A and stevioside can then be treated using the adsorb/desorb separation process of the invention (see, FIG. 1) in order to recover additional rebaudioside A. A process overview of such a process is provided in FIG. 2.

In many embodiments, the dry solids portion of the glycoside solution 10 comprises about 20% weight or greater rebaudioside A, for example, about 20% to about 85% weight rebaudioside A, about 40% weight to about 80% weight rebaudioside A, or about 40% to about 60% weight rebaudioside A. Also present in the glycoside solution is stevioside. In many embodiments, stevioside is present up to about 60% weight of the solids component of the glycoside solution, for example, about 10% to about 50% weight stevioside. The glycoside solution may also contain one or more other glycosides, for example, rebaudioside B, rebaudioside C, rebaudioside D, rebaudioside E, rebaudioside F, and dulcoside.

The glycoside solution 10 also comprises a solvent. Solvent compositions for the glycoside solution 10 typically comprise a lower alcohol (e.g., a C1-C3 alcohol) and water. Examples of lower alcohols include methanol, ethanol, and propanol (e.g., n-propanol and i-propanol). Mixtures of two or more alcohols and water may also be used. In many embodiments the solvent composition comprises about 20% weight to about 80% weight lower alcohol and about 20% weight to about 80% weight water, based on the total weight of the solvent composition. More typically, the solvent composition comprises about 30% weight to about 70% weight lower alcohol and about 30% weight to about 70% weight water.

Prior to dilution with the elution solvent 40, the glycoside solution 10 typically comprises about 15% weight to about 50% weight dissolved solids and about 50% to about 85% weight solvent. In some embodiments, the glycoside solution comprises about 30% weight to about 50% weight dissolved solids and about 50% weight to about 70% weight solvent.

In adsorb/desorb separations of the invention, the stationary phase adsorbent 30 comprises a macroporous polystyrene crosslinked with divinylbenzene and functionalized with tertiary amines, quaternary amities, or both tertiary and quaternary amines. The stationary phase adsorbent has a high surface area, for example, about 900 m2/gram or greater, or about 900-1500 m2/gram. Useful stationary phase adsorbents include those commercially available under the trade designation "MACRONET", from Purolite Corporation, Bala Cynwyd, Pa. Representative examples include MACRONET MN100; MN 150; MN170; and MN300, with MN 100 and MN300 being preferred. Selected properties of the MACRONET adsorbents are provided in the table below.

|  |  | MACRONET ™ Resin | | | |
| --- | --- | --- | --- | --- | --- |
| Property | Units | MN100 | MN150 | MN170 | MN300 |
| Surface Area | m²/gram | 900-1100 | 900-1200 | 1000-1500 | 900-1100 |
| d50 (Hg intrusion) | Å | 850-950 | 300-400 | <100 | 850-950 |
| Pore Volume | ml/gram (dry) | 1-1.1 | 0.6-0.8 | 0.2-0.4 | 1-1.1 |
| Functionality |  | WBA | WBA | WBA | WBA |
| Dry Weight Capacity | eq/kg | 0.6-0.8 | 0.4-0.7 | 0.7-1.0 | 1.2-1.4 |

-continued

| Property | Units | MACRONET™ Resin | | | |
|---|---|---|---|---|---|
| | | MN100 | MN150 | MN170 | MN300 |
| Volume Capacity | eq/l | 0.1-0.2 | 0.1-0.3 | 0.3-0.5 | 0.2-0.4 |
| Moisture | % | 58-61 | 52-55 | 30-50 | 58-61 |
| Strong Base Capacity | % | 10-20 | 10-20 | 10-20 | 10-20 |
| Expansion (ionic forms) | % | <5 | <5 | <5 | <5 |

Useful elution solvents 40 comprise ethanol/water solutions, typically comprising up to about 20% weight ethanol in water. If the amount of ethanol is too high, the stevioside may not bind as tightly to the adsorbent. In the process of the invention, the elution solvent 40 mixes with the glycoside solution 10 and the combined solution moves though the adsorbent bed 20 and the stationary phase adsorbent 30. Typically, the elution solvent 40 is combined with the glycoside solution 10 in a weight ratio ranging from about 98:2 to 20:80 (parts elution solvent: parts glycoside solution), more typically ranging from about 96:4 to 60:40 (parts elution solvent: parts glycoside solution).

Figure 1A:
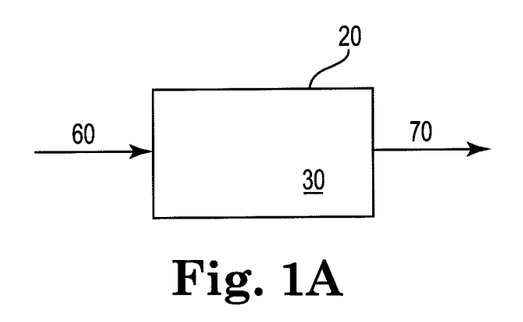
FIG. 1A is schematic representation of the desorption step in an adsorb/desorb separation of the invention.

After conducting the adsorb/desorb chromatographic separation, the adsorbent 30 is typically regenerated in order to remove the bound stevioside from the adsorbent 30. FIG. 1A shows absorbent bed 20 being regenerated by passing regeneration solvent 60 through the bed in order to elute a stevioside-rich elutant 70 from adsorbent bed 20. Typically, the regeneration solvent 60 is an ethanol/water solution that comprises about 50% weight or greater ethanol in water.

Using adsorb/desorb separation an increase in rebaudioside A purity of about 10% weight or greater, about 20% weight or greater, about 25% weight or greater, or about 30% weight or greater as compared to the initial purity of the rebaudioside A material may be achieved. In an absolute measurement, rebaudioside A purifies of 60% weight to about 80% weight may be achieved. For example, using MN300 resin the purity of a rebaudioside A solution increased from 64% weight to 83% weight using 10% volume ethanol/water as the elution solvent. In another example, the purity of a glycoside solution increased from 53% weight to 76% weight under the same conditions. As used herein, purity refers to the grams rebaudioside A per 100 grams of rebaudioside A plus stevioside. Rebaudioside A recovery rates of about 80% or greater or 90% or greater may be achieved.

In some embodiments of the invention the adsorb/desorb separation may be conducted multiple times in order to increase the final purity of the rebaudioside A. For example, the purified rebaudioside A solution from a first adsorb/desorb separation may be fed into a second chromatography bed in order to further purify the rebaudioside A solution.

Fractionation Separations:

In some embodiments of the invention, the separation takes place using fractionation type chromatography. Fractionation chromatography involves the separation of different components based on relatively small differences in affinity to a stationary phase adsorbent. The different affinities for the stationary phase cause the components to move through the adsorbent at different propagation velocities leading to the desired separation.

Figure 3:
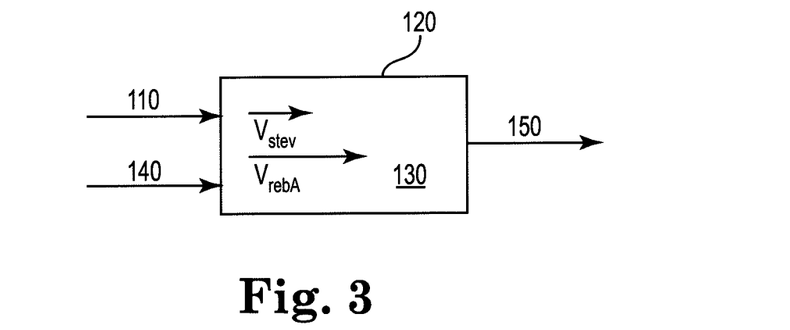
FIG. 3 is a schematic representation of a fractionation separation of the invention.

An exemplary embodiment of fractionation chromatography is shown in FIG. 3. In FIG. 3 a glycoside solution 110 containing rebaudioside A and stevioside is fed to an adsorbent bed 120. The adsorbent bed contains a stationary phase adsorbent 130. An elution solvent 140 is fed though the adsorbent bed along with the glycoside solution 110. The elution solvent 140 functions to transport the glycoside solution 110 through the adsorbent bed 120 and the stationary phase adsorbent 130. While moving through the absorbent 130, the stevioside that is present in the glycoside solution 110 adsorbs more strongly to the stationary phase adsorbent 130 than the rebaudioside A that is also present in the glycoside solution 110. This causes the stevioside to move through the stationary phase adsorbent 130 at a slower rate than the rate of rebaudioside A. That is, the propagation velocity of stevioside ($v_{stev}$) though the stationary phase adsorbent 130 is slower than the propagation velocity of the rebaudioside A ($v_{reb\,A}$) though the stationary phase adsorbent 130. This results in a separation between stevioside and rebaudioside A allowing a purified rebaudioside A solution to be collected at effluent 150.

In some embodiments of the invention, fractionation chromatography is performed using a continuous process known as simulated moving bed chromatography (SMB). In simulated moving bed chromatography, a flow of liquid mobile phase moves countercurrent to a flow of an adsorbent. The flow of the adsorbent is accomplished by packing the adsorbent into a series of columns which are moved relative to the flow of the liquid mobile phase. Useful simulated moving bed chromatography devices are commercially available from SepTor Technologies B.V. (The Netherlands) or from Calgon Carbon Corp.

FIG. 4 provides a process flow diagram for a typical simulated moving bed chromatographic separation of a glycoside solution. In FIG. 4 the simulated moving bed apparatus 200 includes chromatography zone 210, chromatography zone 220, chromatography zone 230, and chromatography zone 240. Each chromatography zone may include one or more packed chromatographic columns, typically 1 to 9 columns, more typically 1 to 6 columns. Chromatography zones 210, 220, 230, and 240 are in fluid communication with one another via connections 250. In operation of the SMB process, a glycoside solution 260 is introduced into chromatography zone 230 at the point labeled "Feed". The glycoside solution flows though the chromatography zones in the direction shown by arrow 270 labeled "Fluid Flow". At the same time as the glycoside solution is flowing in the direction shown by arrow 270, the chromatography zones 210, 220, 230, and 240 are moved in the direction shown by arrow 280 labeled "Resin". The flow rates of the glycoside solution 270 and the adsorbent in chromatography zones 210-240 are adjusted so that the rebaudioside A moves in the direction shown by arrows 290 labeled "Rebaudioside A" and the stevioside moves in the direction shown by arrows 300 labeled "Stew". In operation of the SMB process shown in FIG. 4, a purified rebaudioside A solution is collected from chromatography zone 230 at the point 310 labeled "Product". In order to remove the stevioside from the simulated moving bed process a desorbant solution 320 is introduced into chromatography zone 210 at the point labeled "Desorbant". The desorbant and the purified stevioside solution are collected at point 330 labeled "Byproduct".

As in adsorb/desorb separations, the glycoside solution 110, 260 may be a solution prepared from stevia after primary processing, or the glycoside solution 110, 260 may be the mother liquor of a rebaudioside A crystallization process.

In many embodiments, the dissolved solid portion of the glycoside solution 110, 260 comprises about 20% weight or greater rebaudioside A, for example, about 20% to about 85% weight rebaudioside A, about 40% weight to about 80% weight rebaudioside A, or about 40% to about 60% weight rebaudioside A. Stevioside is also present in the glycoside solution. In some embodiments, stevioside is present up to about 60% weight of the solids component of the glycoside solution, for example, about 10% to about 50% weight stevioside. The glycoside solution may also contain one or more other glycosides, for example, rebaudioside B, rebaudioside C, rebaudioside D, rebaudioside E, rebaudioside F, and dulcoside.

Solvent compositions for the glycoside solution 110, 260 typically comprise a lower alcohol (e.g., a C1-C3 alcohol) and water. Examples of lower alcohols include methanol, ethanol, and propanol (e.g., n-propanol and i-propanol). Mixtures of two or more alcohols and water may also be used. In many embodiments the solvent composition comprises about 20% weight to about 80% weight lower alcohol and about 20% weight to about 80% weight water, based on the total weight of the solvent composition. More typically, the solvent composition comprises about 30% weight to about 70% weight lower alcohol and about 30% weight to about 70% weight water. In exemplary embodiments, the solvent composition comprises about 40% weight to about 60% weight lower alcohol and about 40% weight to about 60% weight water, or about 45% weight to about 55% weight lower alcohol and about 45% weight to about 55% weight water.

The glycoside solution 110, 260 typically comprises about 15% weight to about 50% weight dissolved solids and about 50% to about 85% weight solvent. In some embodiments, the glycoside solution comprises about 30% weight to about 50% weight dissolved solids and about 50% weight to about 70% weight solvent.

In fractionation separations, the stationary phase adsorbent 130, 230 may comprise a macroporous polystyrene crosslinked with divinylbenzene and functionalized with tertiary and/or quaternary amines. In some embodiments, the stationary phase adsorbent has a high surface area, for example, about 900 m2/gram or greater, or about 900-1500 m2/gram. Useful stationary phase adsorbents include those commercially available under the trade designation "MACRONET" from Purolite Corporation, Bala Cynwyd, Pa. and are described hereinabove. Representative examples include MACRONET MN100; MN 150; MN170; and MN300. Also useful as the stationary phase absorbent 130, 230 in fractionation separations are strongly acidic cationic exchange resins, for example, Rohm & Haas Amberlite™ CR1310 Ca; Mitsubishi UBK555 and Dowex™ 99.

Useful elution solvents 140 comprise 0 to 20% weight ethanol in water. Typically, the elution solvent is combined with the glycoside solution 10 in a volume ratio ranging from about 98:2 to 20:80 (parts elution solvent: parts glycoside solution), more typically ranging from about 96:4 to 60:40 (parts elution solvent: parts glycoside solution).

In another embodiment, as shown in FIG. 5, the simulated moving bed apparatus includes 6 chromatography zones and collection points for 4 products. In FIG. 5 the simulated moving bed apparatus 500 includes chromatography zones 510, 515, 520, 530, 535, and 540. Each chromatography zone may include one or more packed chromatographic columns, typically 1 to 9 columns, more typically 1 to 6 columns. Chromatography zones 510, 515, 520, 530, and 540 are in fluid communication with one another via connections 550. In operation of the SMB process, a glycoside solution 560 is introduced into chromatography zone 530 at the point labeled "Feed". The glycoside solution 560 flows though the chromatography zones in the direction shown by arrow 570 labeled "Fluid Flow". At the same time as the glycoside solution 560 is flowing in the direction shown by arrow 570, the chromatography zones 510, 515, 520, 530, and 540 are moved in the direction shown by arrow 580 labeled "Resin".

Because the steviol glycosides have different affinities for the resin, a separation of a mixture of these glycosides into four distinct streams enriched in each glycoside is possible. The four products, in order of increasing affinity for the resin, are rebaudioside B, rebaudioside A, stevioside, and rebaudioside D. The chromatography system to produce 4-product streams is similar in many respects to that disclosed in FIG. 4, with the following modifications. Two additional chromatography zones are added to the system, zones Ia 515 and IIIa 535, to allow for the separation of rebaudioside D and rebaudioside B at the points 610 and 640, respectively, labeled "RebD" and "RebB". Zone Ia 515 desorbs glycosides with sufficient desorbant 520 to only desorb the lower affinity stevioside, while retaining the rebaudioside D on the resin. The rebaudioside D is then desorbed in Zone I 510. Zone II 520 and Zone III 530 operate in the same manner as described in FIG. 4. Zone IIIa 535 is added to allow for the desorption of the lower affinity rebaudioside B at the point 640 labeled "RebB", independent from rebaudioside A 630. The feed and desorbant flow rates and the bed switching times are chosen such that the individual glycosides migrate in the simulated moving bed apparatus as shown in streams 660, 670, 680, and 690. By contrast, in FIG. 4, the rebaudioside D is eluted with the stevioside and the rebaudioside B is eluted with the rebaudioside A. The feed and desorbant flow rates and the bed switching times are chosen such that the rebaudioside A and stevioside migrate as shown in 670 and 680. The feed and desorbant flow rates and the bed switching times are similar to the 2-product fractionation system of FIG. 4. This embodiment enables the processing of materials containing elevated levels of rebaudioside B and rebaudioside D without impact the quality of the rebaudioside A or stevioside streams. It could also be used to make pure product of rebaudioside D and rebaudioside B.

In another embodiment, the process as described above and illustrated in FIG. 5 may be used to produce 3 products. By removing sections Ia or IIIa, a mixture of steviol glycosides could be separated into fractions enriches in any subset of rebaudioside A, rebaudioside B, rebaudioside D, or stevioside.

The process of the invention can be employed to enrich a composition of glycosides containing a subset of rebaudioside A, rebaudioside B, rebaudioside D, and stevioside. Raw materials typically seen contain up to 5% by weight rebaudioside D (more typically 1-3% by weight) and up to 15% by weight rebaudioside B (more typically 2-8% by weight). Additionally, in-process glycoside streams recovered from other processes (e.g., crystallization) containing rebaudioside B levels up to 40% (more typically 12-35% by weight) may be enriched using this process.

Using fractionation an increase in rebaudioside A purity of about 10% weight or greater, about 20% weight or greater, about 25% weight or greater, or about 30% weight or greater as compared to the initial purity of the rebaudioside A material may be achieved. In an absolute measurement, rebaudioside A purities of 60% weight to about 80% weight may be achieved. As used herein, purity refers to the grams rebaudioside A per 100 grams of rebaudioside A plus stevioside. Rebaudioside A recovery rates of about 80% or greater or 90% or greater may be achieved. Fractionation has the potential to lead to higher recovery and/or purity than adsorb/desorb chromatography.

The invention will now be described with reference to the following non-limiting examples.

EXAMPLES

Example 1

Adsorb/Desorb Chromatography

A solution of 10 wt % ethanol and 90 wt % water containing a glycoside mixture at a total concentration of 6% solids (glycoside composition: rebaudioside A 42%, Stevioside 38%, Other glycosides 20% by weight) was contacted with MN100 resin at 60 C. One bed volume of glycoside solution was passed through the resin at a rate of one bed volume per hour. Following this loading, 3.5 bed volumes of 10 wt % ethanol were passed through the column at a rate of one bed volume per hour and gathered to result in a solution containing glycosides 69% rebaudioside A, 31% stevioside and other glycosides. 93% of the rebaudioside A fed to the column was recovered in the purified stream. The remaining glycosides remained bound to the column until treated with two bed volumes of 50 wt % ethanol elutant to remove the stevioside-rich stream.

Example 2

Adsorb/Desorb Chromatography

A 1-inch (I.D.) heat jacketed glass column was packed with 215 mL of standard-grade (mean particle size 450-620 um) Purolite MN100 resin by the slurry method using deionized water and then the column was heated to 55 degrees C. using a circulating water bath. The resin was conditioned by eluting with four (4) bed volumes of deionized water followed by two (2) bed volumes of 10 vol % ethanol. About 12.9 grams of a crude glycoside containing about 43 wt % rebaudioside-A and about 40 wt % stevioside was then dissolved in 1 bed volume (215 mL) of 10 vol % ethanol to produce a glycoside solution containing about 6.0 grams glycoside per 100 mL of solvent. The glycoside solution was pumped at a flow rate of about 3.8 mL/min to the top of the column using a peristaltic pump. Once the glycoside solution was delivered, elution was continued by addition of 1.6 bed volumes (about 344 mL) of 10 vol % ethanol to collect the rebaudioside-A enriched fraction. This process delivered a rebaudioside-A enriched fraction containing about 62 wt % rebaudioside-A and 18 wt % stevioside. A stevioside enriched fraction was then collected by desorbing the bound glycosides with 3 bed volumes (645 mL) of 50 vol % ethanol. Desorption with 50 vol % ethanol delivered a stevioside enriched fraction containing about 56 wt % stevioside and about 28 wt % rebaudioside-A. Overall, rebaudioside-A mass recovery was about 63 wt % in the rebaudioside-A enriched fraction and about 29 wt % in the stevioside enriched fraction.

Example 3

Fractionation Chromatography

A 1-inch (I.D.) heat-jacketed glass column was packed with 225 mL of standard-grade (mean particle size 450-620 um) Purolite MN100 resin by the slurry method using deionized water and then the column was heated to 55 degrees C. using a circulating water bath. The resin was conditioned by eluting with four (4) bed volumes of deionized water followed by two (2) bed volumes of 35 vol % ethanol. About 4.1 grams of a crude glycoside containing about 65 wt % rebaudioside-A and about 22 wt % stevioside was then dissolved in 0.1 bed volumes (22.5 mL) of 35 vol % ethanol to produce a glycoside solution containing about 18.2 grams glycoside per 100 mL of solvent. The glycoside solution was pumped at a flow rate of about 1.9 mL/min to the top of the column using a peristaltic pump. Once the glycoside solution was delivered, elution was continued using 35 vol % ethanol. About 82 wt % of the rebaudioside-A mass was recovered in the 1st bed volume and its purity was about 80 wt % rebaudioside-A and 13 wt % stevioside.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of separating rebaudioside A from stevioside using chromatography, the method comprising the steps of:
    (a) providing a glycoside solution comprising rebaudioside A; stevioside; and a solvent;
    (b) providing an adsorbent comprising a polystyrene divinylbenzene support functionalized with tertiary amines, quaternary amines, or both tertiary and quaternary amines; and
    (c) contacting the adsorbent with the glycoside solution in order to separate at least a portion of the rebaudioside A from the stevioside thereby resulting in the formation of a purified rebaudioside A solution.

2. The method of claim 1, wherein the method of separating comprises adsorb/desorb chromatography.

3. The method of claim 2, wherein the adsorb/desorb chromatography comprises the steps of
    (a) providing a glycoside solution comprising rebaudioside A; stevioside; and a solvent;
    (b) providing an adsorbent comprising a polystyrene divinylbenzene support functionalized with tertiary amines, quaternary mines, or both tertiary and quaternary amines;
    (c) providing an elution solvent;
    (d) contacting the adsorbent with the glycoside solution and elution solvent so that at least a portion of the stevioside adsorbs onto the adsorbent enriching the glycoside solution in rebaudioside A and resulting in the formation of a purified rebaudioside A composition that is eluted from the adsorbent along with the elution solvent; and
    (e) optionally, desorbing the stevioside from the adsorbent.

4. The method of claim 3, wherein the elution solvent comprises about 20% weight or less ethanol; and about 80% weight or greater water.

5. The method of claim 3, wherein the elution solvent comprises about 50% weight or less ethanol; and about 50% weight or greater water.

6. The method of claim 1, wherein the method of separating comprises fractionation chromatography.

7. The method of claim 6, wherein the fractionation chromatography comprises the steps of:
   (a) providing a glycoside solution comprising rebaudioside A; stevioside; and a solvent;
   (b) providing an adsorbent comprising a polystyrene divinylbenzene support functionalized with tertiary amines, quaternary mines, or both tertiary and quaternary amines; and
   (c) contacting the adsorbent with the glycoside solution so that at least a portion of the stevioside adsorbs onto the adsorbent and so that at least a portion of the rebaudioside A adsorbs onto the adsorbent; wherein the rebaudioside A propagates through the adsorbent at a faster rate than the stevioside; and
   (d) collecting a purified rebaudioside A solution from the adsorbent.

8. The method of claim 7, wherein the solvent comprises about 20% weight or greater ethanol and about 80% weight or less water.

9. The method of claim 7, wherein the solvent comprises about 25% to about 35% weight ethanol and about 65% to about 75% water.

10. The method of claim 7, wherein the solvent comprises water and wherein the adsorbent is a strongly acidic cationic exchange resin.

11. The method of claim 7, wherein the glycoside solution further comprises one or more glycoside selected from rebaudioside B and rebaudioside D; and wherein the method provides a separation between stevioside, rebaudioside A, rebaudioside B, and rebaudioside D.

12. The method of claim 11, wherein the method provides a separation between stevioside, rebaudioside A, rebaudioside B, and rebaudioside D.

13. The method of claim 6, wherein the fractionation chromatography is performed using a simulated moving bed.

14. The method of claim 1, wherein the adsorbent has a surface area of about 900 m2/gram or greater.

15. The method of claim 1, wherein the adsorbent is functionalized with tertiary amines.

16. The method of claim 1, wherein the adsorbent is functionalized with quaternary amines.

17. The method of claim 1, wherein the glycoside solution is a mother liquor from a rebaudioside A crystallization process.

18. The method of claim 1, wherein the purified rebaudioside A solution has a purity that is about 10% or greater as compared to a purity of the glycoside solution.

19. The method of claim 1, wherein the purified rebaudioside A solution comprises, on a dry solids basis, about 60% weight to about 80% weight rebaudioside A.

20. The method of claim 1, wherein the glycoside solution further comprises one or more glycosides selected from rebaudioside B, rebaudioside C, rebaudioside D, rebaudioside E, rebaudioside F, and dulcoside.

21. The method of claim 20, wherein the glycoside solution comprises one or more glycosides selected from rebaudioside B and rebaudioside D.

* * * * *

UNITED STATES PATENT AND TRADEMARK OFFICE
CERTIFICATE OF CORRECTION

Page 1 of 1

PATENT NO. : 9,005,444 B2
APPLICATION NO. : 12/992843
DATED : April 14, 2015
INVENTOR(S) : Chiang et al.

It is certified that error appears in the above-identified patent and that said Letters Patent is hereby corrected as shown below:

In the specification

Column 2, line 11, delete "mines," and insert -- amines, --, therefor.

Column 2, line 32, after "quaternary", delete "mines," and insert -- amines, --, therefor.

In the claims

Column 10, line 42, claim 3, after "steps of" insert -- : --.

Column 10, line 48, claim 3, after "quaternary", delete "mines," and insert -- amines, --, therefor.

Column 11, line 7, claim 7, after "quaternary", delete "mines," and insert -- amines, --, therefor.

Signed and Sealed this
Third Day of November, 2015

Michelle K. Lee
*Director of the United States Patent and Trademark Office*